United States Patent [19]

Dumaine et al.

[11] Patent Number: 5,251,825

[45] Date of Patent: Oct. 12, 1993

[54] METHOD AND APPARATUS FOR COMMINUTING AND DECONTAMINATING WASTE MATERIAL

[75] Inventors: Thomas J. Dumaine, North Attleboro, Mass.; John E. Kennett, North Kingstown; Michael G. Kelly, East Greenwich, both of R.I.

[73] Assignee: Mediclean Technology, Inc., West Warwick, R.I.

[21] Appl. No.: 963,137

[22] Filed: Oct. 19, 1992

[51] Int. Cl.⁵ .................. B02C 19/12; B02C 23/18
[52] U.S. Cl. ........................ 241/16; 241/38; 241/606; 241/DIG. 38
[58] Field of Search ............... 241/16, 38, 21, 606, 241/DIG. 38; 422/32, 105, 107, 119

[56] References Cited

U.S. PATENT DOCUMENTS

| | | | |
|---|---|---|---|
| 4,809,915 | 3/1989 | Koffsky et al. | 241/36 |
| 5,001,425 | 3/1991 | Beling et al. | |
| 5,064,124 | 11/1991 | Chang | 241/33 |
| 5,078,965 | 1/1992 | Pearson | 422/3 |
| 5,087,420 | 2/1992 | Jackson | 422/37 |
| 5,089,228 | 2/1992 | Meijer | |
| 5,116,574 | 5/1992 | Pearson | 422/3 |
| 5,130,092 | 7/1992 | Liu | 422/28 |

FOREIGN PATENT DOCUMENTS 2038298  10/1991  Canada .

*Primary Examiner*—Mark Rosenbaum
*Assistant Examiner*—John M. Husar
*Attorney, Agent, or Firm*—Lahive & Cockfield

[57] ABSTRACT

A method and apparatus for comminuting and decontaminating discrete batches of waste material to reduce the volume, to render it unrecognizable and to render it safe for subsequent handling. The minimum volume of decontaminant fluid to be added to each batch is determined by its weight. Batches of differing weights are fed consecutively to the comminuting apparatus either manually or by a conveyor. A batch weigh scale is employed to preset a timer which controls the duration of operation of a device feeding decontaminant fluid to the batch. The feeding means can be made operable to withdraw reactive agents from separate storage means, to mix them to produce the decontaminant fluid and to feed the reacted mixture into the comminuting apparatus.

17 Claims, 3 Drawing Sheets

METHOD AND APPARATUS FOR COMMINUTING AND DECONTAMINATING WASTE MATERIAL

SUMMARY OF THE INVENTION

This invention relates generally to methods and apparatus for comminuting and decontaminating waste materials, and more particularly to processes and apparatus for controlled generation of decontaminants and dispensing thereof into the waste materials as they are being comminuted.

An important but not exclusive use of the invention is the treatment of regulated medical waste. This waste comprises a wide variety of objects and substances of a non-reuseable nature that are required to be reduced in volume, made unrecognizable and treated to be made safe for subsequent handling. Typically, specifications call for such materials to be mechanically reduced to small, unrecognizable particles suitable for bulk handling, for example particles that will pass through a ⅜ inch classifier screen. The materials must also be decontaminated, typically by dispensing decontaminants into the materials before and/or after they have been comminuted.

As used herein, the term "comminution" refers generally to the process of fragmenting the materials to reduce their volume or size, and includes without limitation such methods as granulation, shredding, dicing, pelletizing, grinding, slicing and triturating. In the presently preferred embodiments we employ a granulator as hereinafter described.

Waste comminuting apparatus of the foregoing type is frequently and preferably installed near the sources of waste production. The apparatus may be used on an irregular or intermittent basis, and the skill level of available operating personnel often precludes the use of sophisticated measurements and controls.

One object of this invention is to provide a method and apparatus for generation of the decontaminants at the site of the apparatus. In particular, it is desirable to avoid the necessity of shipping large volumes of prepared decontaminants to the site and of storing the prepared decontaminants there prior to use. This is particularly important with the use of decontaminants having a limited shelf life.

The waste materials are preferably placed in bags or other discrete disposable containers as the normal first step in disposal within a hospital or similar institution. The nature, weight and volume of materials in the bags may vary widely, and thus the volume of decontaminant required for effective decontamination of each bag is similarly variable. Another object of this invention is to provide methods and apparatus to ensure adequate decontamination of all comminuted materials according to a prescribed specification. Such a specification should typically provide for an effective decontaminating dosage measured in grams of the active ingredient per gram of the waste material, and also for an effective concentration of the active ingredient in grams per unit weight of the solvent or other fluid vehicle.

A further object of the invention is to provide methods and apparatus suitable for various sizes of installations and weight rates of comminution per unit of time.

With the above and other objects in view, the features of this invention include a method by which the weights of discrete batches of waste materials are measured prior to feeding them successively into the hopper chamber of the comminuting apparatus. Each measured weight is used to compute a "flow time" interval during which a prepared decontaminating treatment fluid is fed into the batch as it is being comminuted. The fluid is fed at a predetermined volume or weight rate and contains a predetermined concentration of the active ingredient. The computed time interval is that required to deliver a prescribed dose of the active decontaminating ingredient, as above defined, to the particular batch.

The computed time interval for feeding of the treatment fluid corresponds to the minimum time required for the prescribed dose of the active ingredient. According to another feature of the invention, this minimum interval may be exceeded with particular batches according to a predetermined algorithm or algorithms.

Another feature of this invention includes the provision of waste comminuting apparatus having means for measurement of the weights of discrete batches of waste materials prior to their feeding or placement into the hopper chamber of the comminuting apparatus. A weigh scale produces a weight signal for automatic computation of the "flow time" interval of feeding of decontaminating treatment fluid into the apparatus for each corresponding batch. Thus the minimum weight or volume of decontaminant may be determined proportionately to the weight of each corresponding discrete batch of waste as it is being processed through the apparatus.

The employment of controls based on batch feeding ensures accurate control of the rate of decontaminant generation and feed whether the materials are fed to the comminuting apparatus on a relatively continuous or on a variable intermittent basis.

Another feature is that the method is well adapted for on-site production of the decontaminant when employed with appropriate proportional metering pumps, valves and controls associated with plural reactive agent storage means.

Variants of the method and apparatus of this invention are adapted for either large or small installations, with uniform accuracy and reliability in the dispensing of decontaminants into the comminuted materials.

Other features of the invention will become evident from the following description of the Presently preferred embodiments, having reference to the appended drawings.

DETAILED DESCRIPTION

Figure 1:
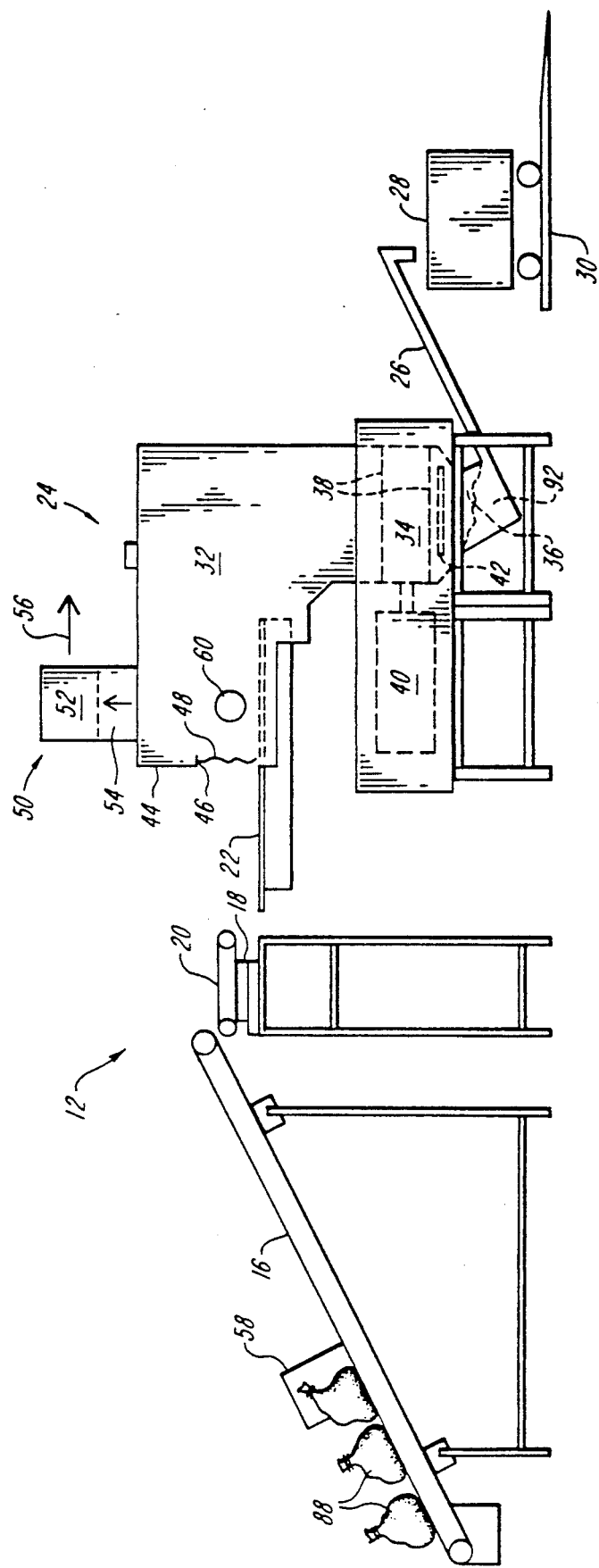
FIG. 1 is a schematic illustration of the presently preferred form of the invention, illustrated in a configuration for large volume rates of material comminution, in this embodiment by granulation.
Figure 2:
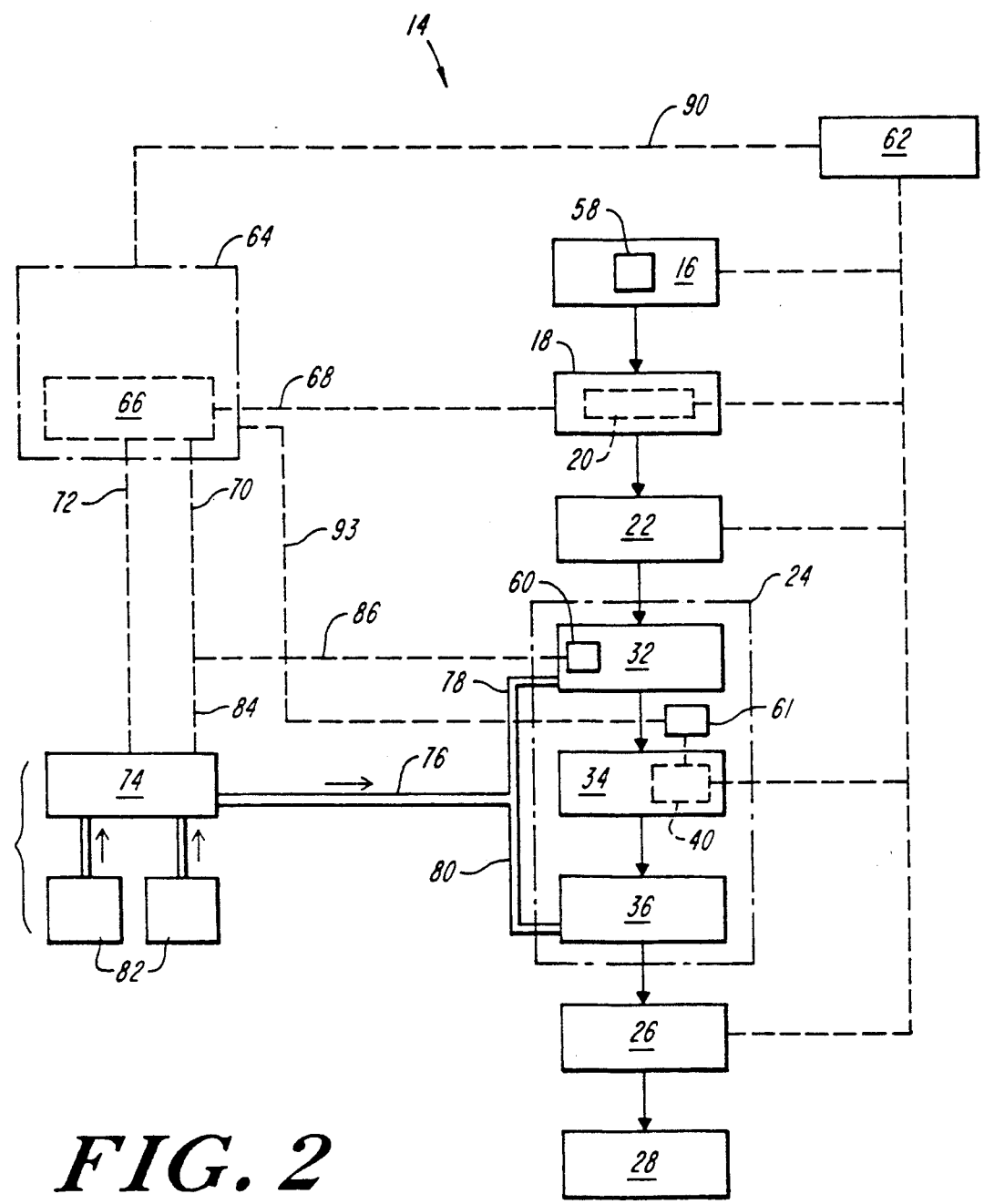
FIG. 2 is a block diagram showing the controls associated with the apparatus of FIG. 1.

Apparatus for granulation and decontamination of waste material according to this invention is depicted in FIG. 1 generally at 12. Controls for operation of this apparatus are depicted in FIG. 2 generally at 14. The apparatus 12 comprises an inclined conveyor 16, preferably a cleat conveyor, a weigh scale 18 supporting a belt conveyor 20, a vibratory pan feeder 22 of conventional form, a granulator assembly 24, a screw auger 26, and a waste receptacle 28. Optionally, the receptacle 28 stands on a scale 30 which may be fitted with controls (not shown) for interrupting the power to the apparatus 12 when the receptacle 28 is full.

The granulator assembly 24 is preferably a rotating knife granulator of the type described in the copending United States application of Thomas J. Dumaine Ser. No. 772,280, filed Oct. 7, 1991, now U.S. Pat. No. 5,195,685 dated Mar. 23, 1993. The main components comprise a hopper chamber 32, a granulating chamber 34 and a receiving chamber 36. The apparatus within the granulating chamber comprises a number of rotating, axially extending knives 38 driven by a motor 40, and one or more fixed bed knives (not shown), the particles severed between the rotating and bed knives falling through a classifier screen 42 into the receiving chamber 36. It will be apparent, however, that the practice of this invention is not limited to the use of granulating apparatus, and other forms of comminuting equipment may be substituted as appropriate.

The hopper chamber is formed with a hood 44 having an aperture 46. The vibratory pan feeder extends into the aperture 46 and outwardly of the hood 44 to a position for receiving waste material from the conveyor 20. The use of a feeder of the vibratory type is preferred over a belt conveyor because it does not require portions thereof to move from the interior of the hood, which is subjected to contaminated fragments and particles, to the exterior of the apparatus. Preferably, the aperture 46 has a flexible fabric closure flap 48 or suspended ribbons of flexible sheet material which tend to retard the flow of air through the aperture, yielding inwardly to the waste materials passing into the hopper chamber on the feeder 22.

An air filter assembly 50 is mounted on the hood of the hopper chamber, preferably in the vicinity of the aperture 46. This assembly comprises a fan 52 and a filter 54. The preferred filter is a high efficiency particulate air filter comprising a commercially available extended surface, deep bedded, randomly positioned fibrous material. During operation of the apparatus the fan 52 expels air from the hopper chamber in the direction of the arrow 56, thereby maintaining an air draft through the aperture 46 into the hopper chamber and through the filter 54. Thus any particles generated by the granulating apparatus and suspended in the air within the hood are diverted from direct passage through the aperture 46 into the ambient air space, and are trapped in the filter.

The controls 14 for the apparatus 12 of FIG. 1 are schematically illustrated in FIG. 2. These controls preferably include a material detector 58 located in position to detect the presence of certain substances that may be present in the waste materials on the conveyor 16, for example metal or radioactive materials. They also preferably include a material sensor 60 located in front of or within the hopper chamber 32 in position to detect the presence of waste materials entering or approaching the hopper. The sensor 60 may be a photosensor or any other commercially available device for detecting the presence of the materials.

The controls further preferably include an ammeter 61 for measuring the current drawn by the motor 40, which indicates by a drop in value that the granulation of a batch has been completed. For convenience, the term "running time" as used herein means the length of time required for the entire contents of a batch to pass from the hopper 32 through the granulating chamber 34 into the receiving chamber 36. This may be automatically detected by the ammeter 61, or alternatively by a suitable torque measuring device mechanically connected with the drive shaft of the motor 40.

Referring to FIG. 2, like reference numerals indicate the corresponding elements of FIG. 1. A power source 62 is provided for driving the conveyors 16 and 20, the feeder 22, the granulator motor 40 and the screw auger 26.

The apparatus is operated by a control unit 64. In this embodiment the control unit essentially comprises a microprocessor and a programmable logic controller, both of which are of a commercially available form. However, relays or other types of controls having similar functions may be substituted, as will be evident to those skilled in the art. The unit 64 preferably includes circuits and detectors for monitoring numerous functions of the apparatus 12 for convenience and safety in operation, such elements being omitted from this description where considered to be within the scope of conventional practice. An element pertinent to this invention comprises a timer 66 provided with a "preset" connection 68, a "start" connection 70 and a "stop" connection 72. The "preset" connection extends to the weigh scale 18, whereby the magnitude of the weight on the scale presets the timer to operate for a "flow time" interval, measured from an "on" pulse on the connection 70, proportional to the measured weight. At the end of this "flow time" interval the timer produces an "off" pulse on the connection 72.

A metering device 74 is connected with a source of decontaminant fluid, and feeds the fluid through lines 76, 78 and 80 into the hopper and receiving chambers of the granulator 24. The device 74 is adapted to feed the decontaminant fluid at a uniform controlled volume rate which, when properly adjusted, normally remains constant during operation of the apparatus. It may take the form of a valve openable to cause water under municipal water pressure to flow at a predetermined rate as the vehicle for an aqueous solution of an active decontaminating ingredient. Alternatively, it may take the form of a pump having a predetermined rate of delivery. The device 74 can be connected with a single source of fully prepared decontaminant fluid, if desired, but preferably it is connected with two or more reactive agent storage means 82, and is adapted by means of valves and other conventional means to withdraw the agents therefrom in predetermined proportions, mixing the agents with the fluid vehicle to react them and to produce a fluid with the desired concentration of the active ingredient, thereafter feeding it through the line 76. The use of plural agent storage means permits the on-site generation of decontaminant, and thus the decontaminant fluid is generated only when needed and only in the quantities necessary for controlled decontamination of the waste materials passing through the apparatus 12. The device 74 is operated by a signal on an "on" connection 84 and stopped by an "off" signal on the connection 72. The "on" signal is transmitted by a connection 86 from the material sensor 60, and simultaneously starts the timer 66 and the device 74.

The operation of the apparatus 12 under the action of the controls 14 is next described. Bags 88 filled with regulated medical waste are typically made of disposable plastic material, often color-coded according to the nature of the waste contents, and containing differing volumes and weights of differing kinds of waste materials. The control unit 64 starts the apparatus by a signal on a connection 90 and the bags 88 are manually or automatically loaded in single file sequence on the inclined conveyor 16. The bags pass the detector 58 which, for example, detects the presence of a metal within any bag. If metal is present the detector 58 stops the conveyor 16 and the bag is manually removed. If desired, the detector 58 may detect the presence of a radioactive substance, or other materials to be excluded from the granulation process.

The bags 88 are delivered consecutively to the conveyor 20 supported on the weigh scale 18. The weight of a bag on this conveyor is transmitted over the connection 68 to preset the timer 66 for the corresponding "flow time." From the conveyor 20 the bag falls upon the vibratory pan feeder 22 and is transported through the aperture 46 into the hopper chamber 32. When the presence of the bag is detected by the material sensor 60, an "on" signal passes over the connection 86 to start the timer 66 and the device 74.

The device 74 initiates the generation and feeding of decontaminant fluid at a controlled, constant volume rate, whereby the bag 88 is immediately subjected to a portion of the decontaminant fluid injected into the hopper chamber, immediately falling into the granulating chamber where the contents are simultaneously reduced to small particles and mixed with the decontaminant. The particles fall through the classifier screen 42 and into the receiving chamber 36, into which a further portion of decontaminant fluid is injected by the device 74. A body 92 of ground and decontaminated waste is thereby produced at the receiving end of the screw auger 26. The auger carries this waste product to the receptacle 28. Alternatively, the screw auger may carry the waste product to a dewatering unit or system from which the fluid component flows to a sewer and the solids component is delivered to a suitable receptacle.

The timed duration of operation of the device 74, and therefore the total volume of decontaminant fluid pumped into the contents of the bag 88, corresponds to the value preset into the timer 66. This in turn corresponds to the weight of the bag and its contents detected by the weigh scale 18. By this means the volume of decontaminant fluid used can be automatically made proportional to the weight of the waste materials, thereby producing the predetermined or required dosage measured in units of weight of the active ingredient per unit of weight of the waste material.

Conditions may arise when it is desired to add to a given batch more than the volume of decontaminant fluid that would be fed in the computed "flow time." This may be accomplished by including one or more suitable algorithms in the functions of the control unit 64. In this embodiment the unit 64 measures the "running time" of a batch, that is, the time required for all material in a given batch to be comminuted. For this purpose information representing the length of time that the current measured by the ammeter 61 remains at an elevated level is transmitted over a connection 93 to the unit 64. The unit 64 computes the ratio of this "running time" to the computed "flow time" of operation of the device 74. If the ratio exceeds a given value, for example 1.5, the unit 64 is set to cause the device 74 to operate and feed one or more bursts of additional fluid to the granulator immediately following the "flow time" as determined by the weight of the batch.

Apparatus in the configuration of FIG. 1 can be designed to process bags or other discrete bodies of waste materials at a large volume rate and with minimal operator involvement except that required for loading the materials on the conveyor 16 and periodically removing the waste receptacle 28. Operator attention to the weighing of bags, and the proportional mixing of agents and dosage of the fluid disinfectant, is not required.

In settings where relatively lower volume rates of waste materials are being processed, the inclined conveyor 16, the conveyor 20 on the weigh scale 18 and the vibratory pan feeder 22 may be omitted. In this case the hopper chamber may be reconfigured for manual loading of the bags of waste material by an operator. Controls suitable for this mode of operation are shown generally at 94 in FIG. 3. In this figure like reference numerals refer to the corresponding elements in FIGS. 1 and 2, and operate as described with reference to that figure.

Figure 3:
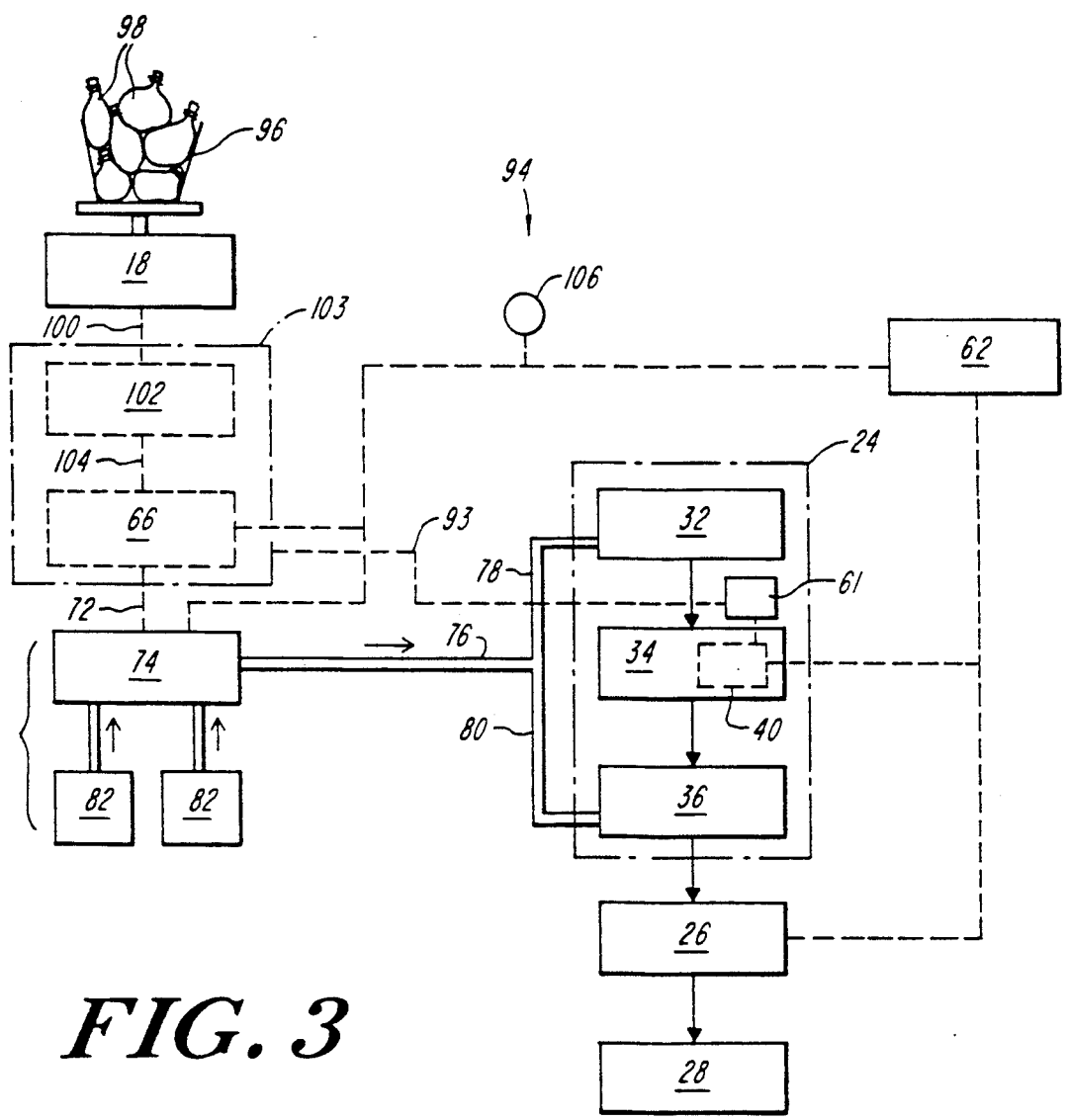
FIG. 3 is a block diagram representing modified controls for portions of the apparatus of FIG. 1, particularly adapted for smaller volume rates of material granulation.

In the embodiment of FIG. 3 a cart or other container 96 is placed on the weigh scale 18 with a number of bags 98 of waste material in the container. The initial weight of the container and its entire contents is measured and transmitted by a connection 100 to a weight loss computer 102 preferably comprising a part of a control unit 103. The unit 103 may be similar to the unit 64 except as noted below.

Operation of the apparatus is initiated by the operator by removing one or more of the bags 98 from the container 96 and placement of the bags in the hopper chamber 32. This action produces a new, lower weight signal on the connection 100 to the computer 102, which thereupon computes the difference between the initial and new weights and transmits this difference by a connection 104 to the timer 66, presetting the timer to the corresponding "flow time."

Thereupon, the operator presses an "on" button 106, simultaneously turning on the power source 62, the timer 66 and the device 74. The granulation of the materials in the hopper chamber and the treatment thereof by decontaminant fluid then occurs substantially as described above with reference to FIG. 2.

When the operator notes that the materials loaded into the hopper chamber have been completely or substantially granulated, the process described above is repeated by removal of one or more additional bags 98 from the container 96 and placement thereof in the hopper chamber 32. In each repetition of the process, the volume of decontaminant fluid pumped into the hopper and receiving chamber corresponds to the weight loss of the container 96 and contents, which equals the weight of all of the bags simultaneously loaded into the hopper chamber, the number of such bags being within the discretion of the operator.

In some installations it may be satisfactory to eliminate certain of the automatic functions described above with reference to the weigh scale 18 of FIG. 2 or the weigh scale 18 of FIG. 3, including related connections thereof to the control units 64 or 103 and certain functions of these control units. For example, an operator may visually observe the weight of each batch and enter the weight into the control unit 64 or 103 by means of a keypad or equivalent device. Also, since the "flow time" computed from the measured weight is either proportional to such weight as described herein, or may be some other predetermined function of such weight, the operator may readily determine the "flow time" from the visually observed weight on the scale by simple computation or by consulting a function table or graphic chart, and may directly preset the timer 66 to the corresponding "flow time." It is also possible to provide a dial face on the weigh scale which is calibrated directly in units of "flow time" instead of units of weight, with the "flow time" units being directly entered to preset the timer by means of a keypad or the like. As noted above, the control units 64 and 103 Preferably include, in addition to the elements hereinabove described, other detecting circuits, indicators and limiting devices to prevent unsafe conditions from arising and to ensure the smooth flow of materials through the apparatus. For example, means may be provided to detect the depletion of the contents of any of the agent storage means 82. Excess power consumption by the granulating equipment as detected by the ammeter 61 or similar device, overloading of any of the other apparatus components, and malfunctions of valves or other controls associated with the device 74, may be detected. Any of these conditions may cause the unit 64 to interrupt the operation of the apparatus and to establish a "fail-safe" condition until the malfunction has been corrected.

We claim:

1. A method of comminuting and decontaminating waste material comprising the steps of
    dividing the material into discrete batches,
    separately measuring the weight of a batch,
    computing a dosage of a decontaminate fluid as a function of the weight of said batch, said dosage being of sufficient volume to decontaminate said batch,
    loading said batch into a comminuting apparatus while substantially simultaneously applying said dosage to the material in said apparatus,
    discharging the comminuted material from said apparatus, and
    repeating the foregoing steps for said batches sequentially.

2. The method of claim 1, in which said decontaminate fluid is applied to said material in said apparatus in a flow time which is substantially proportional to the measured weight of the batch.

3. The method of claim 1, in which the feeding of said fluid includes withdrawal of plural agents from separate storage means and mixture thereof to form said fluid of a predetermined composition.

4. The method of claim 3, in which said agents are mutually reactive to form an active ingredient, and said fluid is formed with a predetermined concentration of said ingredient.

5. Apparatus for comminution and decontamination of discrete batches of waste material comprising, in combination,
    a weigh scale adapted to produce a weight signal representing the weight of a batch of said material thereon,
    a comminuting apparatus,
    means operable to convey said batch from the weigh scale to said apparatus,
    means responsive to the weight signal for computing a dosage of a decontaminate fluid as a function of the weight of said batch, said dosage being of sufficient volume to decontaminate said batch,
    decontaminate fluid flow means operable to apply a volume of decontaminate fluid into said batch, and
    control means responsive to said computing means to time the operation of said decontaminate fluid flow means as said function of said weight.

6. Apparatus according to claim 5, including plural agent storage means, said decontaminate fluid flow means being operable to withdraw agents from said storage means and to mix them in a predetermined proportion to form said decontaminate fluid.

7. Apparatus according to claim 6, in which said decontaminate fluid flow means is adapted to cause said agents to be mutually reactive to form an active ingredient in said decontaminate fluid.

8. Apparatus according to claim 5, in which the decontaminate fluid flow means is operable at a predetermined flow rate and the control means is adapted to control the time duration of operation of the decontaminate fluid flow means as a function of the weight signal.

9. Apparatus according to claim 8, in which the control means includes a timer having means operable in response to the weight signal to preset a decontaminate flow time interval therein, and including
    means to initiate simultaneously the operation of the timer and the decontaminate fluid flow means, the timer having means to interrupt operation of the decontaminant fluid flow means at the end of said flow time interval.

10. Apparatus according to claim 9, in which said means to initiate operation comprises a batch detector responsive to a batch being conveyed to said apparatus.

11. Apparatus for comminution and decontamination of discrete batches of waste material comprising, in combination,
    a comminuting apparatus for receiving a batch,
    means for computing a dosage of a decontaminate fluid as a function of the weight of a batch,
    flow means operable to apply said decontaminate fluid to said material at a predetermined flow rate,
    a timer having means responsive to the computing means to preset a flow time interval therein, and
    means to initiate substantially simultaneously the operation of the decontaminate fluid flow means and the timer, the timer having means to interrupt operation of the decontaminate fluid flow means at the end of said flow time interval.

12. Apparatus according to claim 11, including
    plural agent storage means, said decontaminate fluid flow means being operable to withdraw agents from said storage means and to mix them in a predetermined proportion to form said decontaminate fluid.

13. Apparatus according to claim 12, in which said flow means is adapted to cause said agents to be mutually reactive to form an active ingredient in decontaminate fluid.

14. Apparatus according to claim 11, including
    a weigh scale adapted to produce a weight signal corresponding to a weight thereon, and
    means responsive to a change in said weight signal to produce a loss of weight signal and to preset the timer to a decontaminate fluid flow time interval corresponding to the loss of weight signal.

15. Apparatus according o claim 14 wherein the loss of weight signal is substantially equivalent to the weight of the batch being processed.

16. Apparatus according to claim 11, in which said means to initiate operation also initiates operation of the comminuting apparatus, and including means to measure the running time required to comminute the batch, means to compare said running time with said decontaminate fluid flow time interval, and means to operate the flow means after said decontaminate fluid flow time interval in response to a predetermined value of said comparison.

17. The method of claim 1 including the step of computing the flow time required at a preselected rate to achieve said volume of decontaminate fluid.

* * * * *